US008945924B2

(12) United States Patent
Fuhr et al.

(10) Patent No.: US 8,945,924 B2
(45) Date of Patent: Feb. 3, 2015

(54) PROCESS AND CULTURING UNIT FOR CULTURING BIOLOGICAL CELLS (75) Inventors: Günter R. Fuhr, Berlin (DE); Hagen Von Briesen, Hünstetten (DE); Erwin Gorjup, Saarbrücken (DE); Charli Kruse, Herrnburg (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 1369 days.

(21) Appl. No.: 12/278,903

(22) PCT Filed: Feb. 7, 2007

(86) PCT No.: PCT/EP2007/001041
§ 371 (c)(1),
(2), (4) Date: Aug. 8, 2008

(87) PCT Pub. No.: WO2007/090629
PCT Pub. Date: Aug. 16, 2007

(65) Prior Publication Data
US 2009/0029470 A1    Jan. 29, 2009

(30) Foreign Application Priority Data

Feb. 10, 2006   (DE) ................. 10 2006 006 269

(51) Int. Cl.
C12N 5/00        (2006.01)
C12M 1/12        (2006.01)
(52) U.S. Cl.
CPC .............. *C12M 25/16* (2013.01); *C12M 25/02* (2013.01)
USPC ............................. 435/401; 435/397; 435/325
(58) Field of Classification Search
None
See application file for complete search history.

(56) References Cited

U.S. PATENT DOCUMENTS

| | | | |
|---|---|---|---|
| 4,514,500 A | | 4/1985 | Giaever et al. |
| 5,989,913 A | * | 11/1999 | Anderson et al. ............. 435/394 |
| 6,855,542 B2 | * | 2/2005 | DiMilla et al. ............. 435/289.1 |
| 7,041,505 B2 | * | 5/2006 | Tsuzuki et al. ............... 435/401 |
| 7,704,741 B2 | * | 4/2010 | Fuhr et al. ..................... 435/400 |
| 2003/0194802 A1 | * | 10/2003 | Itskovitz-Eldor et al. .... 435/366 |
| 2005/0058632 A1 | * | 3/2005 | Hedrick et al. ............... 424/93.7 |

FOREIGN PATENT DOCUMENTS

| | | |
|---|---|---|
| EP | 0085573 A2 | 8/1983 |
| WO | 9721801 A2 | 6/1997 |
| WO | 0198517 A2 | 12/2001 |
| WO | 02088329 A1 | 11/2002 |
| WO | WO 2004074425 A2 * | 9/2004 |
| WO | 2005113750 A2 | 12/2005 |

OTHER PUBLICATIONS

Hooker et al. Cultivation of plant cells in aqueous two-phase polymer systems. Plant Cell Reports, vol. 8, pp. 546-549, 1990.*
Aplin et al. Development of cytotrophoblast columns from explanted first-trimester human placental villi: Role of fibronectin and integrin alpha5beta1. Biology of Reproduction, vol. 60, pp. 828-838, 1999.*
Frondoza et al. Human chondrocytes proliferate and produce matrix components in microcarrier suspension culture. Biomaterials, vol. 17, pp. 879-888, 1996.*
Antov et al., "Production of pectinases by *Polyporus squamosus* in aqueous two-phase system", Enzyme and Microbial Technology, vol. 28 (2001), pp. 467-472.
Clarke et al., "Enhancement and repression of the volumetric oxygen transfer coefficient through hydrocarbon addition and its influence on oxygen transfer rate in stirred tank bioreactors", Biochemical Engineering Journal, vol. 28, pp. 237-242, 2006.
Daugulis, "Partioning bioreactors", Current Opinion in Biotechnology (1997), pp. 169-174.
Galindo et al., "Study of Drop and Bubble Sizes in a Simulated Mycelial Fermentation Broth of Up to Four Phases", Biotechnology and Bioengineering, vol. 69, No. 2 (2000), pp. 213-221.
MacLeod et al., "Interfacial effects in a two-phase partitioning bioreactor: degradation of polycyclic aromatic hydrocarbons (PAHs) by a hydrophobic *Mycobacterium*", Process Biochemistry, vol. 40 (2005), pp. 1799-1805.
Schmaijohann et al., "Thermo-Responsive PNiPAAm-g-PEG Films for Controlled Cell Detachment", Biomacromolecules, vol. 4 (2003), pp. 1733-1739.
Zijlstra et al., "Extractive bioconversions in aqueous two-phase systems", Current Opinion in Biotechnology, vol. 9 (1998), pp. 171-176.
International Search Report for PCT/EP2007/001041, mailed Apr. 11, 2007.

* cited by examiner

*Primary Examiner* — Jennifer Dunston
(74) *Attorney, Agent, or Firm* — Caesar, Rivise, Bernstein, Cohen & Pokotilow, Ltd.

(57) ABSTRACT

A targeted cultivation phase adjustment is provided in a process for the cultivation of cells in which biological cells are cultivated on at least one boundary surface between different, non-solid cultivation phases so that pre-determined cultivation conditions are given. A cultivation apparatus (100) for biological cells is also provided that includes a culture container (10) with different, non-solid cultivation phases (20) between which at least one boundary surface is formed.

18 Claims, 9 Drawing Sheets

PROCESS AND CULTURING UNIT FOR CULTURING BIOLOGICAL CELLS

BACKGROUND OF THE INVENTION

The invention relates to a process for the cultivation of biological cells in a non-solid cultivation environment, especially a process for the cultivation of cells, in which biological cells are arranged on at least one boundary surface between liquid and/or gaseous cultivation phases, and to a cultivation apparatus for carrying out such a process.

The cultivation (growth, multiplication and/or differentiation) of biological cells takes place in the practice typically on solid surfaces such as, e.g., on the bottom of a Petri dish or on other cultivation substrates. During the growth in an in vitro cell culture cell monolayers or layered tissue formations form on the solid surface whose form corresponds to the shape of the surface. The cultivation on solid surfaces has the disadvantage that the cells in the cellular union develop under geometric conditions that are determined by the shape of the surface of the cultivation substrate and as a rule do not correspond to the natural conditions. The formation of natural structures in the cellular union is hindered by the cellular culture being shaped by the shape of the surface. A further disadvantage of the in vitro cultivation on a solid surface results from the molecular adhesion of the cells to the surface. Adherent bonds are formed between the cells and the surface by adhesive proteins, e.g., of the integrin family, that must be loosened during manipulations of the cellular culture. For example, a transfer of cells onto another substrate requires an enzymatic treatment, e.g., with trypsin or a mechanical scratching off of the cells from the surface. In both instances a significant stress for the cells and a cellular loss cannot be avoided.

In order to avoid the shaping of the cellular culture by the surface shape of a solid substrate, DE 10 2004 025 086.3 describes the use of a host egg as incubator for in vitro cultures. This advantageously creates cultivation conditions that come the closest to the natural growth conditions as regards the geometric conditions and the supply of nutrients. However, this technique has the disadvantage that the environmental conditions during the cultivation of cells are given by the properties of the host egg used.

Figures 30, 31:
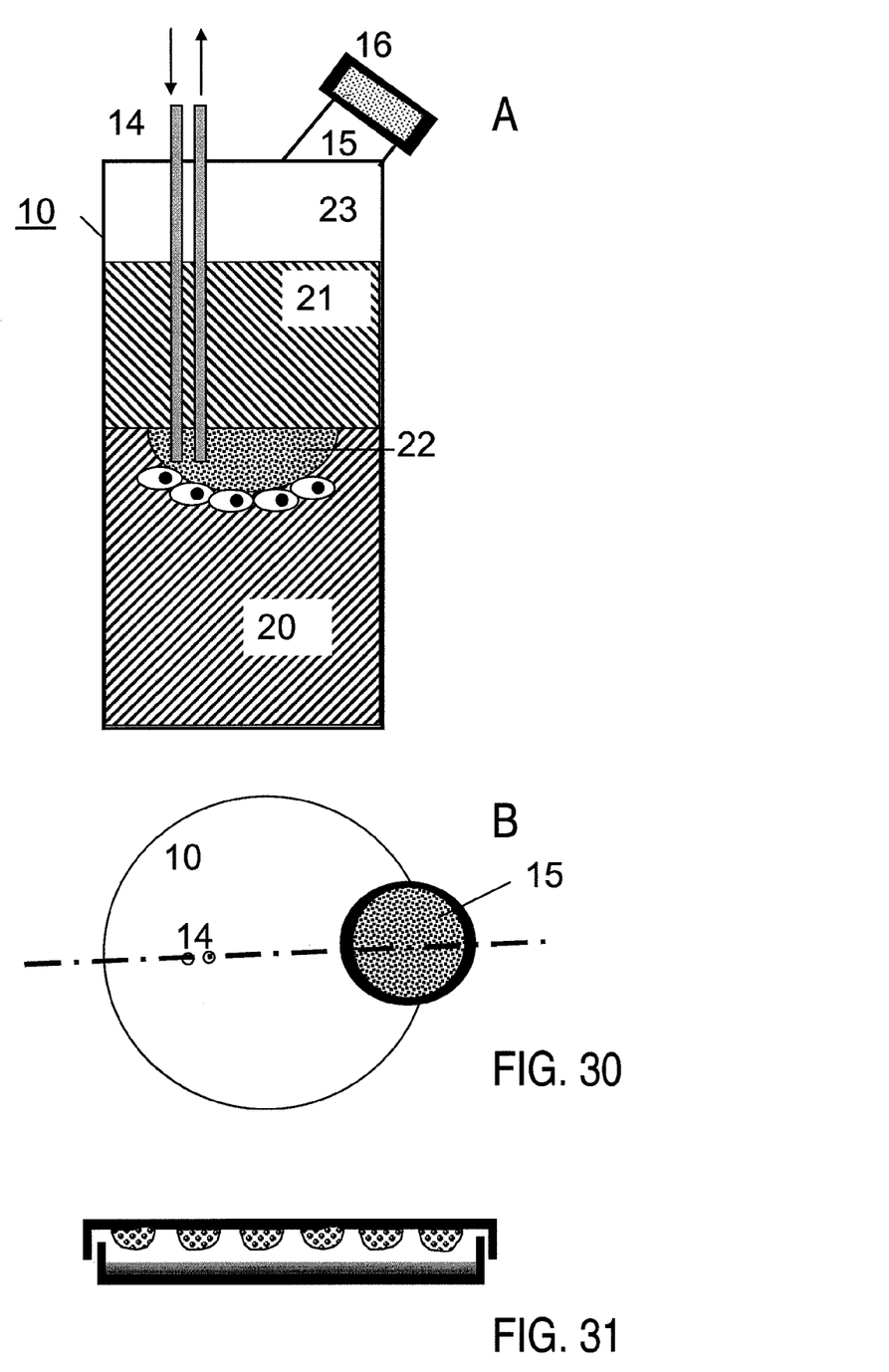
FIG. 31 shows an illustration of the conventional cell cultivation in suspended drops.

The cultivation of individual cells or cellular groups in suspended drops of a liquid cultivation medium as is schematically shown in FIG. 31 is known from the practice of the cultivation of stem cells. Conditions are advantageously given in the suspended drop that are similar to the geometric conditions of the growth, e.g., in an egg. The cells can freely move in the liquid cultivation medium on the curved inner surface of the suspended drop and form cell groups or cell unions. However, a decisive disadvantage of this technique resides in the limited size of the suspended drops. The drops can only have diameters up to a few millimeters so that the cultivation time and the size of the cultivated cell groups are correspondingly limited.

The holding of cell cultures in bioreactors (diffusion reactors, fermenters) is known in order to obtain substances that are produced by the cells (see, for example, G. M. Zijlstra et al. in "Current opinion in biotechnology", volume 9, 1998, pp. 171-176; C. T. MacLeod et al. in "Process Biochemistry", volume 40, 2005, pp. 1799-1805; A. J. Daugulis in "Current opinion in biotechnology", volume 8, 1997, pp. 169-174; M. G. Antov et al. in "Enzyme Microbial. Technol.", volume 28, 2001, pp. 467-472; and K. G. Clarke et al. in "Biochem. Eng. J." volume 28, 2006, pp. 237-242). Typically, a liquid multiphase system of several immiscible phases is contained in a bioreactor and substances produced by the cells in a first phase diffuse into an adjacent phase and are removed from there. Accordingly, a retroaction of the substances on the cells in the first phase is avoided. The use of the conventional bioreactors is limited to biotechnological functions such as, for example, the production of substances. Cultivation conditions can be adjusted with a bioreactor under which the cells are viable and produce the desired substance. However, the conventional bioreactors are not suitable for cultivation tasks of the cellular biology such as, for example, the above-cited cultivation of cells in the cellular union.

The invention has the objective of providing an improved process for the cultivation of biological cells with which the disadvantages of the conventional cultivation techniques are overcome. The process should make a cell cultivation possible, in particular under conditions that are not influenced by the shape or size of a cultivation container and at the same time make possible an adaptation to natural conditions of the growth, the multiplication and/or the differentiation of cells. Furthermore, the objective of the invention is to provide a cultivation apparatus with which the disadvantages of the conventional cultivation apparatuses for the in vitro cultivation of biological cells are overcome.

These objectives are solved by a cell cultivation process or a cultivation apparatus of the invention.

SUMMARY OF THE INVENTION

As concerns the process, the objective of the invention is solved by the general technical teaching of providing predetermined cultivation conditions in a cultivation of biological cells on a boundary surface between non-solid cultivation phases in that the properties of the cultivation phases bordering the boundary surface are adjusted in a targeted manner. Cultivation conditions are advantageously adjusted that are suited for influencing the differentiation of the cells. As concerns the apparatuses, the objective of the invention is solved by a cultivation apparatus with a culture container that contains at least two non-solid cultivation phases between which a pre-determined boundary surface is formed. According to the invention, at least one boundary surface is advantageously formed by the targeted adjustment of the cultivation phases on which boundary surface the biological cells arrange themselves during the cell cultivation. The at least one boundary surface preferably serves as substrate. In distinction to the conventional cultivation on solid surfaces the cells can be readily separated from the boundary surface. The disadvantages of the surface adhesion, e.g., for a cell transfer, are excluded. In contrast to the conventional cultivation of cells in a host egg the cultivation conditions are provided by adjusting the cultivation phases. The limitation to the geometric and material cultivation conditions that were given in the conventional technique by the natural egg form is overcome. Accordingly, even the limitations in size of the conventional cultivation in suspended drops are overcome.

The cultivation apparatus is preferably artificially produced, that is, composed of components that do not cooperate in the nature.

The term "cultivation phase" designates an area in the culture container here that is materially homogeneous and delimited against the environment. The cultivation phase has a determined volumetric form. The cultivation phase is formed by a non-solid medium (so-called cultivation medium) that comprises, e.g., a single chemical compound or a chemical substance composition. The non-solid cultivation phase consists of a gaseous medium or of a flowable, especially liquid medium. Cultivation phases serve for the formation of the at least one boundary surface and optionally for the supply of nutrients to the cells such as, e.g., the supply of oxygen or carbon dioxide by the gaseous cultivation phase or the supply of growth factors by the liquid cultivation phase. A first cultivation phase can completely include or encase several further cultivation phases. Accordingly, an outer inclusive cultivation phase can be a surrounding solution in which the at least one further cultivation phase is embedded.

The term "cultivation conditions" designates the surrounding conditions of the cells on the at least one boundary surface between the cultivation phases, especially the conditions of the growth, the multiplication and/or of the differentiation. Pre-determined cultivation conditions are preferably formed in the cultivation phase adjustment in accordance with the invention that act on a differentiation of the cells (differentiation conditions).

The term "cultivation phase adjustment" designates here the adjusting of pre-determined geometric, physical and/or chemical properties of the cultivation phases. The adjustment of the cultivation phases means a directed change of at least one of the cited properties so that the desired cultivation conditions are given.

In distinction to the conventional cultivation techniques a differentiation and/or ordered (pre-determined) tissue development of cells on boundary surfaces between different non-solid cultivation phases is advantageously realized with the invention. In particular, the cultivation conditions can be adjusted in such a manner that different cell types and/or tissue types are differentiated and/or grow in direct vicinity.

The invention can be advantageously realized with a broad spectrum of different cell types. The cell cultivation takes place especially advantageously with animal cells, especially cells of higher animal classes such as, for example, cells of fishes, mammals or birds, or with human cells. Alternatively, even plant cells can be subjected to the cell cultivation in accordance with the invention.

According to a preferred embodiment of the invention, the cultivation phase adjustment comprises an influencing of the geometric properties of the cultivation phases so that the at least one boundary surface between the cultivation phases receives pre-determined form. If, according to a first variant, at least one plane boundary surface is formed, advantages result for the formation of plane, layered cell cultures. If, according to a second variant of the invention, at least one curved boundary surface is formed, at least one curved substrate for the cell culture is advantageously formed, as developed in in vivo cultures in nature. The cell cultivation can take place in a curved cell union whose geometry is adapted to natural prototypes.

The adjustment of a certain form of the boundary surface between the cultivation phases can comprise a free formation under the action of the surface tension (adjusted in particular with the viscosity and the size of the cultivation phase) or a forced formation by providing a certain wall form of the culture container in which the cultivation phases are arranged.

According to a further advantageous embodiment of the invention, the cultivation phase adjustment comprises an arrangement of the cultivation phases relative to each another in such a manner that the boundary surface has a pre-determined extent (measure of size). The volume of the in vitro cell culture can advantageously be controlled as a function of the concrete requirements of the cultivation task. The cultivation phases can be controlled with volumes from the µl range to the liter range. The in vitro systems are scalable.

According to a further advantageous embodiment of the invention, the cultivation phase adjustment comprises a control of the chemical composition of the cultivation phases.

The cultivation phases are formed with pre-determined gaseous or liquid cultivation media. The control of the chemical composition can influence in the first place the physical interaction (e.g., miscibility) of adjacent cultivation phases and therewith the at least one boundary surface (geometric effect), or in the second place the chemical conditions of the cultivation (chemical effect). In particular, chemical gradients like those significant, e.g., in the embryogenesis, can be advantageously produced and stabilized in the cultivation phases. Furthermore, the chemical composition of adjacent cultivation phases can be selected in such a manner that chemical reactions between the cultivation phases on the boundary surface where the cell cultivation takes place yield pre-determined active substances with which the cell cultivation is influenced.

According to a preferred variant, the cultivation phase adjustment also comprises the supplying of pre-determined additive substances into the cultivation phases in order to control the geometric, physical or chemical properties of the cultivation phases. Additive substances are preferably added with which the density, the viscosity and/or the miscibility of the cultivation phases can be adjusted. A broad plurality of additive substances is available with which the miscibility of liquid cultivation phases is eliminated or hindered which are inert for the biological cells e.g., polymer compounds, gels, oils, in particular silicone oils compatible with cells, sugar compounds, in particular long-chain dextranes, metrizamide, etc., or glycerol.

Additive substances that adjust the viscosity of a cultivation phase such as, e.g., high-molecular sugars that preferably do not change the osmolarity, or gel additives such as, e.g., agar advantageously make possible a significant limitation or complete hindering of a relative movement of different cultivation phases as a consequence of the gravitation. For example, gaseous cultivation phases (gas bubbles) can be stabilized in liquid cultivation phases by additive substances that raise the viscosity.

Adjacent cultivation phases can be adapted to each other with additive substances that control the mass density of a cultivation phase. For example, a cultivation phase can be adjusted to be lighter, with the same mass density or heavier than a surrounding cultivation phase. The boundary surfaces provided for the cell culture can advantageously be exactly positioned and stabilized in their form therewith. This makes possible a reproducible and precise adjustment of the chemical properties of the cultivation phases, e.g., by supplying pre-determined nutrients.

According to the invention, a slow migration of cultivation phases through a surrounding solution or an outer cultivation phase can be provided. This is especially advantageous for the cultivation of cells in vertical gradients.

According to a further variant of the invention, additive substances for eliminating the miscibility can form membranes on the boundary surface between two adjacent cultivation phases such as, e.g., lipid membranes, protein membranes or polymer membranes.

The cultivation apparatus in accordance with the invention preferably comprises an injection apparatus with which liquid or gaseous substances can be introduced into the culture container. The injection apparatus can be advantageously used to supply nutrients and/or additive substances for forming the liquid phases or for stabilizing the liquid phases. According to preferred variants of the invention, the injection apparatus comprises at least one liquid injector and/or at least one gas injector that each comprise an injection line directed from a substance reservoir into the culture container. A separate injector is preferably provided for each substance (nutrient or additive substance). According to a further variant of the invention, the injection apparatus comprises a suspension injector with which suspension liquids can be introduced into the culture container. A suspension liquid comprises, e.g., a cell suspension or a suspension with synthetic particles.

The cultivation apparatus preferably comprises at least one of the following components for the cultivation phase adjustment in accordance with the invention. If a tempering apparatus and/or a moistening apparatus is provided, certain cultivation conditions such as, e.g., the temperature and/or the ambient moisture can advantageously be adjusted in common for all cultivation phases.

If the cultivation apparatus is provided with at least one measuring apparatus the correct deposition of the biological cells on the at least one boundary surface, the progress of the cell cultivation and/or transfer of cells such as, e.g., the removal of cells from the culture container can be monitored. The cultivation phase adjustment can be controlled as a function of measured values of the measuring apparatus. The measuring apparatus preferably comprises at least one probe that is arranged in the culture container in at least one of the cultivation phases and comprises, e.g., a temperature sensor, a chemical sensor or a pH sensor. The temperature, an ion concentration, e.g., the concentration of bivalent ions (e.g., Ca) or pH value can be measured, e.g., in the vicinity of the boundary surface with the probe. Geometric, physical or chemical properties of the cultivation phase can be changed as a function of the at least one measured value.

An important advantage of the invention consists in the variability in the combination of different cultivation phases. If the cells, according to a preferred feature of the invention, are cultivated on a boundary surface between a liquid and a gaseous cultivation phase, advantages can result for a rapid nutrient supply from the gaseous cultivation phase. The cells are preferably arranged on the boundary surface in such a manner that they are completely enclosed by the substance of the liquid cultivation phase. The cells are covered by a liquid film on the side facing the gaseous cultivation phase.

According to an especially preferred embodiment of the invention, the gaseous cultivation phase is surrounded on all sides by the liquid cultivation phase. The gaseous cultivation phase forms a bubble, e.g., in the form of an ellipsoid, enclosed on all sides in the liquid environment. In this variant a concavely curved boundary surface with cultivation conditions similar to the cultivation in the natural egg or in suspended drops is provided; however, the form and size of the boundary surface can be controlled in a purposeful manner in accordance with the invention. For example, the viscosity of the liquid cultivation phase can be adjusted sufficiently high so that the gaseous cultivation phase is maintained stable in the liquid cultivation phase for the duration of the cell cultivation. The gaseous cultivation phase can be provided, e.g., with a cross-sectional dimension selected in the range of 0.05 m to 10 cm.

If the culture container has a sufficient volume, several gaseous cultivation phases can be arranged separately from each other in a common liquid cultivation phase in order to provide several boundary surfaces for the cell cultivation. This embodiment of the invention can be of advantage for the cultivation of rather large cell groups or for the comparison of the cultivation results of different cells.

According to a further advantageous feature of the invention, the cells can be arranged on a boundary surface between two liquid cultivation phases. The substances of the adjacent cultivation phases are preferably selected in such a manner that the cultivation phases can not be mixed with each other. Alternatively, a flexible membrane such as, e.g., a biological double layer can be provided between the cultivation phases.

Liquid cultivation phases can be adjusted in superposed layers, preferably in order to produce plane boundary surfaces.

Alternatively, the liquid cultivation phases can be arranged as in the combination of the gaseous and liquid cultivation phases in such a manner that an at least inner, liquid cultivation phase is completely enclosed by an outer, liquid cultivation phase.

A further preferred embodiment of the invention provides that a physical or chemical phase transition is induced during or at the end of the cell cultivation in at least one of the cultivation phases. Phase transitions in the viscosity or between solid and liquid states can be induced, e.g., under sterile conditions. To this end, polymers are preferably used as substances of the cultivation phases whose properties greatly change as a function of the temperature, e.g., in a range of 5° C. to 40° C., as a function of the pH value or as a function of the ion concentration.

Such polymers can be switched by an adjustment of the temperature, of the ion strength and/or of the pH value from a first into a second conformation. Typically, hydrophobic and/or hydrophilic molecular groups are exposed or screened off in the different states. This is the case, e.g., for polymers that can alternate between a collapsed and an expanded state. Examples for such polymers are poly(N-isopropylacrylamide) (PNiPAA) or Poly(N,N-diethylacylamide) (PDEAAm) (see C. L. McCormick (ed.) in "Stimuli-responsive water-soluble and amphiphilic polymers", ACS Symposium, Series No. 780, American Chemical Society, Washington D.C., 1999). Such polymers can be advantageously synthesized together with functional polymers (e.g., polyethylene glycol, PEG) as copolymers (see D. Schmaljojann in "Langmuir", vol. 4, 2003, S. 1733). Correspondingly, different chemical and/or physical cultivation conditions can be adjusted in the cultivation phases.

According to a further modification, the invention can provide that at least two of the cultivation phases are fused with each other. In order to fuse the cultivation phases the geometric, physical or chemical properties of the participating cultivation phases are adapted until the boundary surface is eliminated and the cultivation phases unite with each other. Cells or cell groups that were at first cultivated separately can be advantageously brought in contact with each other by the fusion of cultivation phases. During the growth of cell cultures and/or the differentiation of cells, cells can influence each other mutually, as is the case in nature, e.g., in the embryogenesis.

Alternatively, a division from a cultivation phase into separate cultivation phases can be provided. This embodiment of the invention advantageously makes it possible that cell culture that was at first cultivated in a uniform manner can be divided into at least two parts as starting point for a further cultivation.

According to a further preferred embodiment of the invention, the cultivation of the biological cells on the boundary surface between non-solid cultivation phases can be influenced by providing a solid substrate body. A gel body, a net, a filament, a textile substrate, a foil or a composition of at least two of these substrate body types is preferably provided as substrate body. The substrate body is preferably distinguished by a flexibility. The substrate body can be adapted to the form of a boundary surface between cultivation phases. According to a further advantageous variant, the substrate body has a lesser density than at least one of the cultivation phases bordering on the boundary surface. In this case the substrate body can float on the boundary surface and/or offer the cells a substrate or serve to compartmentalize (subdivide) cultivation areas. The substrate body can have a perforated surface and comprise, e.g., a perforated grating foil. The cells cultivated on the boundary surface can enter into a compound with the substrate body. This embodiment of the invention is especially advantageous for the purposeful production of cell tissue with a certain form and composition (tissue engineering). In order to form a biocompatible implant the substrate body can have the form of the desired implant and be colonized with the desired cells. The substrate body preferably extends from one cultivation phase into the adjacent cultivation phase. The surface of the substrate is aligned so that it deviates from the boundary surface between the cultivation phases. In this case the cell multiplication and cell differentiation are preferably provided in one of the cultivation phases whereas in the other cultivation phase the growth of the cells is induced on or in the substrate body.

A further important advantage of the invention consists in the simplification of the manipulation of biological cells. According to the invention, a cell removal, a cell grouping and/or a cell supply can be provided in the culture container. The selective removal or insertion of cells can advantageously take place in an especially protective and gentle manner on account of the cultivation on the boundary surface between non-solid cultivation phases. Individual cells, cell groups or tissue can be removed enzyme-free and with low mechanical stress from the cultivation phases or from the boundary surface or inversely supplied to them. Mixed cultures from different cell types like those adapted to the natural conditions during tissue formation can be advantageously produced in a defined manner in a defined and reproducible manner. The differentiation and forming of cellular aggregates or tissue can be induced physiologically or compatibly in a purposeful manner by providing certain neighborhoods of cell types or tissue types.

According to an advantageous embodiment of the invention, the removal of cells or cell groups from the cultivation apparatus can take place in a state in which the cells or cell groups are connected to the substrate body. The substrate body can be removed from the cultivation phases with the cells or cell groups or tissue growing on it.

The cultivation phases are preferably adjusted in a cultivation apparatus with a culture container that is open on a top side or has a closable opening. The culture container preferably has a form-stable wall with which a receptacle for the cultivation phases is formed. According to an especially preferred variant of the invention, the wall of the culture container is manufactured from a non-natural, artificial or synthetic material such as, e.g., plastic, glass or ceramics, semiconductor or metal. In distinction to the conventional techniques the shape of the at least one boundary surface between culture phases is not given by the inner form of the culture container but rather by the cultivation phase adjustment.

BRIEF DESCRIPTION OF SEVERAL VIEWS OF THE DRAWINGS

Further details and advantages of the invention are described in the following with reference made to the attached drawings.

FIGS. 30A and 30B show a further embodiment of a cultivation apparatus in accordance with the invention.

DETAILED DESCRIPTION OF PREFERRED EMBODIMENTS

The cultivation processes illustrated in the figures in an exemplary manner can be carried out with all biological cells that can also be multiplied and/or differentiated with the conventional cultivation techniques. For example, embryonic or adult stem cells of different origin from human or animal organisms or differentiated cells from human or non-human, in particular animal organisms can be cultivated. The illustrated processes were tested, e.g., with genetically modified cells comprising, e.g., cells with an expression of marker genes such as, e.g., LacZ or GFP, cells with a "knockout" gene, cells with a "silencing" gene or genes with a gene overexpression.

In the embodiments shown in FIGS. 1 to 28 the cultivation apparatus 100 comprises in accordance with the invention a culture container 10 in which several cultivation phases 20, 21, 22, . . . are arranged. Although a gaseous cultivation phase is shown in all cases, it does not have to be obligatorily provided. Exclusively liquid cultivation phases can be adjusted in the culture container. The culture container 10 (schematic sectional views) comprises a receptacle, e.g., with a parallelepipedic form, a cylindrical form or another volumetric form that has closed bottom- and side walls 11 (see FIG. 1) and an opening 12 on the top. The opening 12 can optionally be closed with a cover (not shown). The culture container 10 comprises, e.g., a plastic box, plastic bottle or plastic dish or a beaker glass. The volume of the culture container 10 is selected as a function of the concrete cultivation task in the range of, e.g., 0.2 ml to 10 l. The cultivation phases 20, 21, 22, . . . in the culture container 10 can be adjusted in accordance with the invention corresponding to the variants of combinations of them explained in the following.

Figure 1:
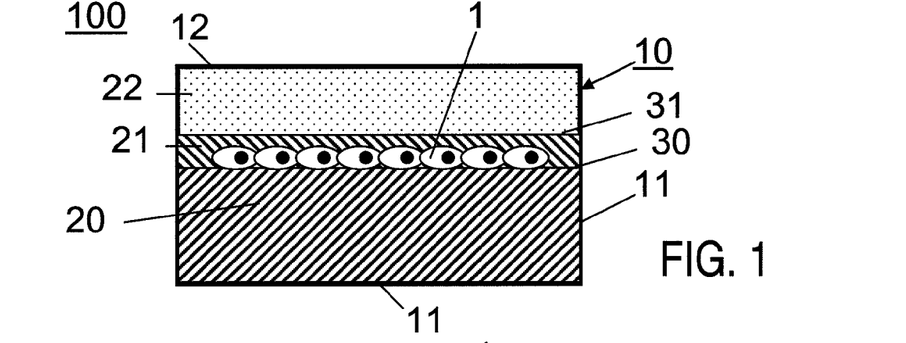
FIGS. 1 to 28 show different embodiments of the adjustment, in accordance with the invention, of cultivation phases for cultivating biological cells.

According to FIG. 1, two liquid cultivation phases 20, 21 and a gaseous cultivation phase 22 are arranged in a layer form in culture container 10. Plane boundary surfaces 30, 31 are formed between the cultivation phases. The liquid cultivation phases 20, 21 comprise immiscible liquid media selected, e.g., from one of the following combinations. The lower liquid cultivation phase 20 typically comprises a carrier liquid such as, e.g., silicone oil, a polymer solution or a gel. The middle liquid cultivation phase 21 preferably comprises a nutrient medium for biological cells. The mass density of the lower cultivation phase is higher than the mass density of the middle cultivation phase and of the cells. The upper gaseous cultivation phase 22 is formed by a volume area in the culture container 10 that is filled with a supply gas or supply vapor such as, e.g., $CO_2$, $O_2$ or the like.

The adjustment of the cultivation phases 20, 21 takes place in such a manner that at first the heavier cultivation phase 20 is filled into the culture container 10 and is subsequently coated over with the lighter cultivation phase 21. The biological cells 1 are introduced into the culture container 10 with the second cultivation phase 21 or during a subsequent injection step with a cell suspension. The cells 1 sink down in the second cultivation phase 21 until they float on the boundary surface 30 on the first cultivation phase 20.

After the adjustment of the cultivation phases 20, 21, 22 with the depositing of the cells 1 on the boundary surface 30 further cultivation conditions such as, e.g., the temperature are adjusted if necessary. To this end a tempering apparatus (see description of FIG. 29) is used with which the temperature of the container can be adjusted.

Figure 2:
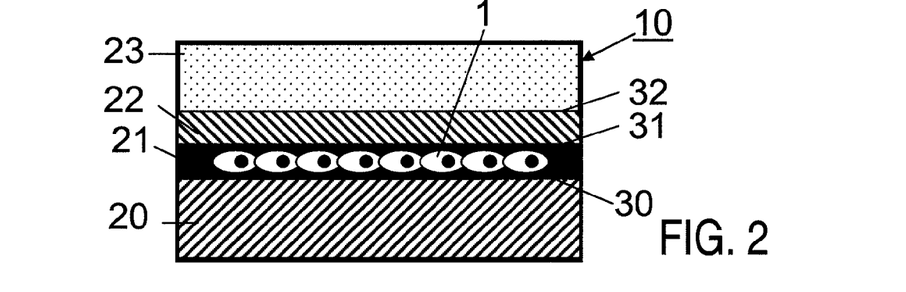

In the embodiment of the invention shown in FIG. 2 three liquid cultivation phases 20, 21, 22 and a gaseous cultivation phase 23 are provided that are arranged in a layer form with level boundary surfaces 30, 31, 32 in the culture container 10. The cells 1 are located in the middle cultivation phase 21, that comprises, e.g., a nutrient medium for the cells and is limited on both sides by the lower and upper cultivation phases 20, 22. The middle cultivation phase 21 forms an almost two-dimensional volume area in a layer form for forming a monolayer of cells 1, e.g., with a thickness of up to 5 mm. Alternatively, larger thicknesses can be provided for producing multi-layer cell cultures.

Figure 3:
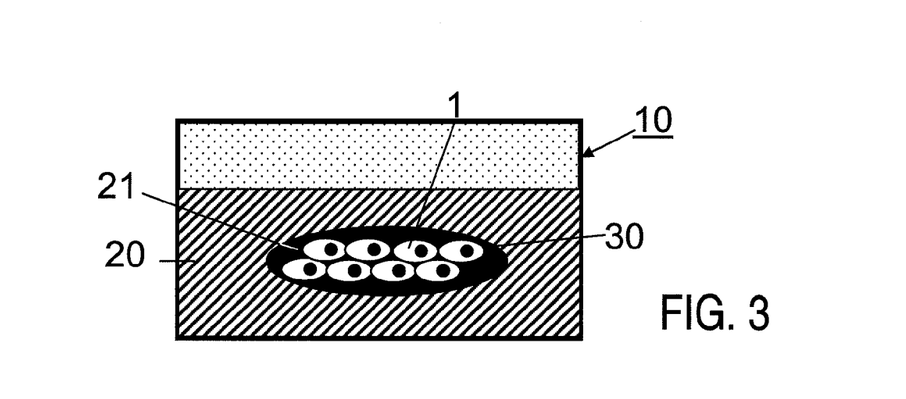
Figure 4:
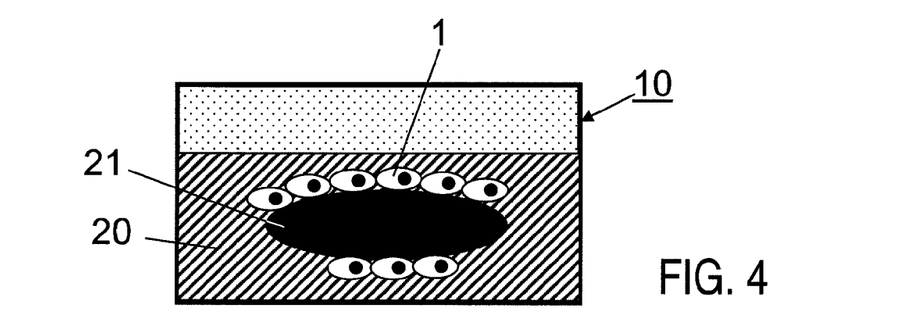

Two liquid cultivation phases 20, 21 with a curved boundary surface 30 are shown in FIGS. 3 and 4. The cells 1 are arranged on the inside (FIG. 3) or outside (FIG. 4) of the boundary surface 30. The substances of the cultivation phases 20, 21 are two flowable, especially liquid compositions that are immiscible but preferably have a similar mass density. For example, according to FIG. 3, the inner liquid phase 21 consists of a nutrient medium surrounded on the outside on all sides by a viscous polymer solution. Alternatively, the nutrient medium can be provided on the outside and the polymer solution on the inside. It is not obligatorily necessary that the cells 1 are arranged in the nutrient medium. If the cells are cultivated on the boundary surface 30, e.g., on the side of the polymer solution, nutrients can diffuse from the nutrient medium through the boundary surface to the cells.

The curved, closed form of the boundary surface 30 shown in FIGS. 3 and 4 advantageously provides geometric cultivation conditions similar to those in a natural host egg or in suspended drops. In distinction to the conventional techniques the size and the form of the boundary surface 30 are adjusted in a purposeful manner as a function of the concrete cultivation task.

FIGS. 5 to 8 illustrate the cultivation of cells 1, 2 with different cell types in differently adjusted cultivation phases analogously to FIGS. 1 to 4. According to FIG. 5, three liquid cultivation phases 20, 21 and 22 are arranged in the culture container 10 in layer form. The cells 1, 2 of the different cell types are cultivated on the boundary surfaces 30, 31 in the cultivation phases 20, 22 spatially separated from one another. The cells grow and differentiate thereby in a spatially separated manner. However, signal substances can be exchanged between the cells 1, 2 by diffusion through the middle cultivation phase 21, e.g., in order to mutually influence the differentiation of the cells. To this end the middle cultivation phase 21 has a thickness preferably in the range of 10 µm to 10 mm.

Figure 6:
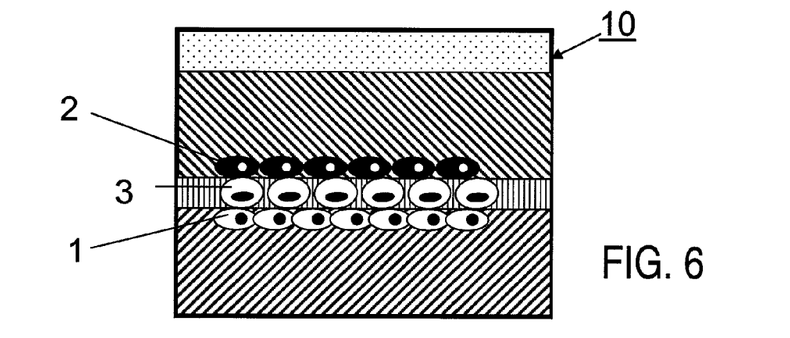

FIG. 6 illustrates the corresponding case with a cultivation of cells 1, 2 and 3 from three different cell types. The cells 3 of the third cell type are cultivated in the middle cultivation phase. The different cell types comprise, e.g., as cells 1 fibroblasts, that act as feeder layer, cells 2 that comprise muscle cells or also fibroblasts, and cells 3 that comprise stem cells or precursor cells, that are to be differentiated during the cultivation.

Figure 7:
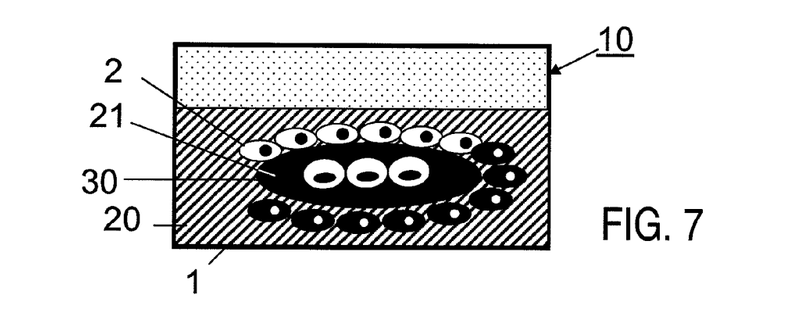
Figure 8:
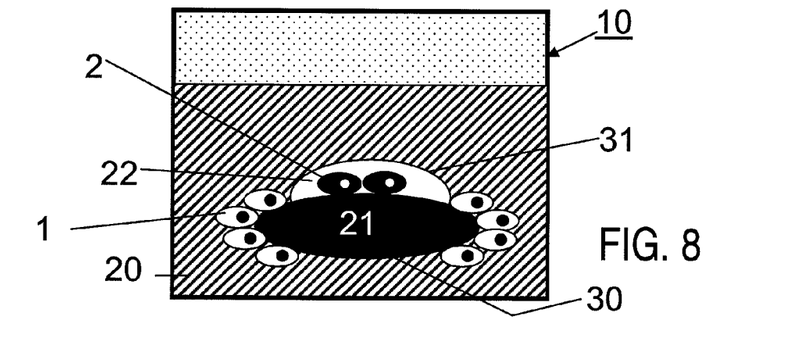

The FIGS. 7 and 8 show the cultivation of different cell types on curved boundary surfaces 30, 31. According to FIG. 7, an immiscible cultivation phase 21 is inserted analogously to FIG. 4 as liquid ellipsoid into the outer cultivation phase 20. The inner cultivation phase 20 can have a higher viscosity than the outer cultivation phase 21 or, e.g., contain protein- and/or nutrient mixtures. Cells 1, 2 of different cell types are arranged on the boundary surface 30 between the cultivation phases 21, 22 whereas cells 3 of a third cell type can grow and differentiate in the inner cultivation phase 21.

In the variant according to FIG. 8, two inner liquid phases 21, 22 are surrounded by the outer liquid phase 22, with curved boundary surfaces 30, 31 being formed. By means of this adjustment of the cultivation phases the cells 1, 2 of different cell types can be spatially separated yet cultivated in mutual interaction in the material diffusion exchange.

Corresponding to the examples shown in FIGS. 5 to 8, more complicated structures of liquid phases can be adjusted in order to cultivate cells of individual or several cell types. Complex cell arrangements can be advantageously constructed therewith whose geometric distribution is selected and held stable in accordance with the distribution of differentiated cells in the germ layers during the course of the embryogenesis. Analogously, complex tissue structures can also be produced from different cells that are finished being differentiated and are multiplied within the framework of the cultivation in accordance with the invention.

The adjustment of the cultivation phases 20, 21, 22 takes place in such a manner that at first the outer cultivation phase 20 is filled into the culture container 10 and subsequently injected with the inner cultivation phase(s) 21 (,22). The biological cells 1 are introduced with the inner cultivation phase or during a subsequent injection step with a cell suspension into the culture container 10.

Figure 5:
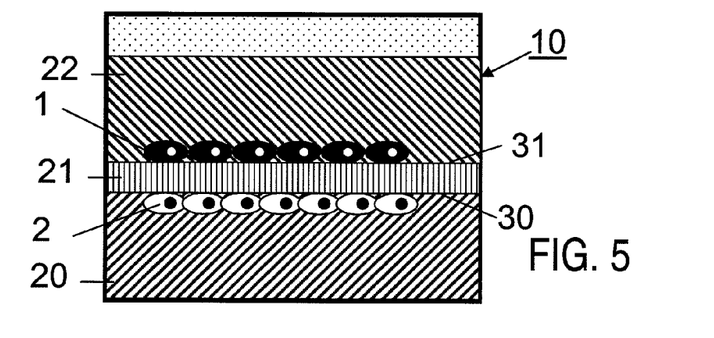
Figure 9:
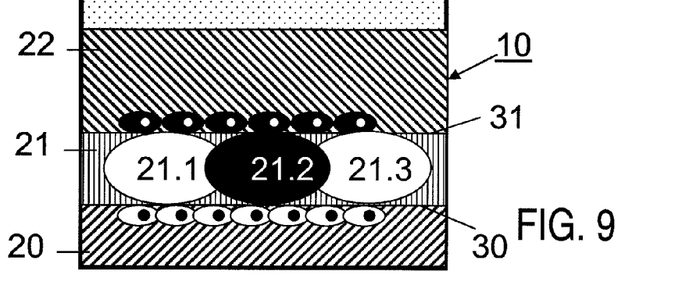

FIG. 9 illustrates a cultivation apparatus 100 with three liquid cultivation phases 20, 21 and 22, arranged as in FIG. 5 in layer form with plane boundary surfaces 30, 31. Additive substances 21.1, 21.2 and 21.3 comprising, e.g., different growth factors, are introduced into the middle liquid phase 21. The growth factors pass by diffusion via the boundary surfaces 30, 31 to the cells 1, 2. Additive substances 21.1, 21.2 and 21.3 can be introduced, e.g., as solid body particles into the middle liquid phase 21. They consist, e.g., of ceramics, gel matrices, tissue- or textile elements or micro- or nanoporous particles with different or the same size.

Figure 10:
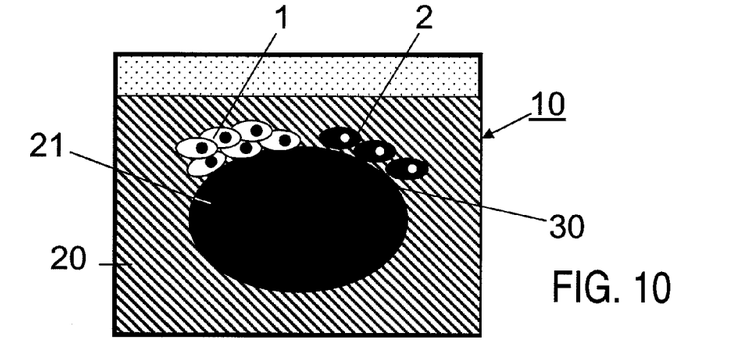
Figure 11:
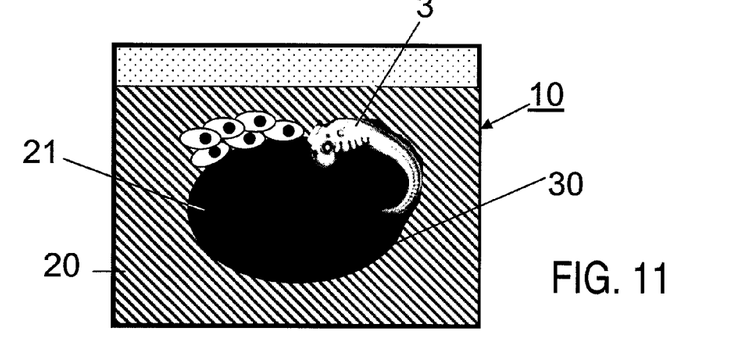
Figure 12:
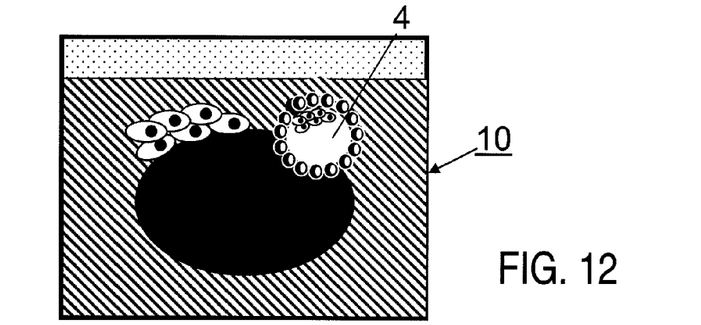
Figure 13:
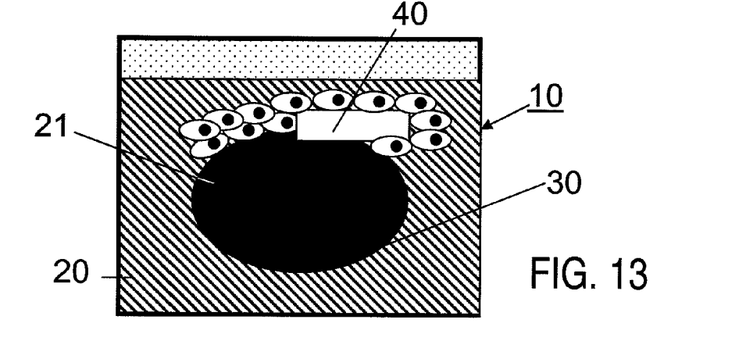
Figure 14:
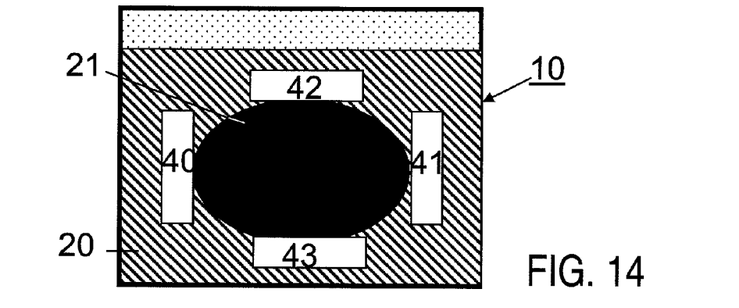

The FIGS. 10 and 11 illustrate the development of complex cell structures on the boundary surface 30 between two liquid cultivation phases 20, 21 analogously to FIG. 4. According to FIG. 10, two cell clusters adjacent to one another are cultivated on the boundary surface 30 that influence one another in their growth- and differentiation behavior. The cells 1, 2 comprise, e.g., adult stem cells, embryonic stem cells, feeder cells, embryonic differentiated cells, adult differentiated cells, tumor cells, egg cells, precursor cells, dendrite cells, fibroblast cells and/or cells of the animal germ disk. The cells can form a loose cell compound or a piece of tissue.

According to FIG. 11, animal cells are cultivated in the vicinity of an embryo or fetus 3 of animal origin (e.g., chicken embryo). The embryo can be replaced according to FIG. 12 by a single cell (oocyte) or zygote or by a cell cluster in a higher division stage up to the blastocyst 4.

The FIGS. 13 to 16 illustrate different variants of the cell cultivation in the presence of a solid substrate body 40, 41, . . . that is to be partially or completely grown over or grown through by the cells cultivated on a boundary surface 30. The substrate body can be a so-called scaffold (carrier structure), e.g., of ceramics, titanium, plastic or other materials customary in the implantation medicine. The substrate body 40, 41, . . . consists, e.g., of a textile fabric, a plastic matrix, a ceramic material, metal, glass or a semiconductor. For example, a bone implant, cartilage implant or heart valve implant can be arranged in the liquid cultivation phases 20, 21 as substrate body. According to FIG. 14, several substrate bodies 40-43 are arranged in pre-determined relative positions in order to be grown around by the cells (not shown) that are cultivated on the boundary surface 30 between the cultivation phases 20, 21.

Figure 15:
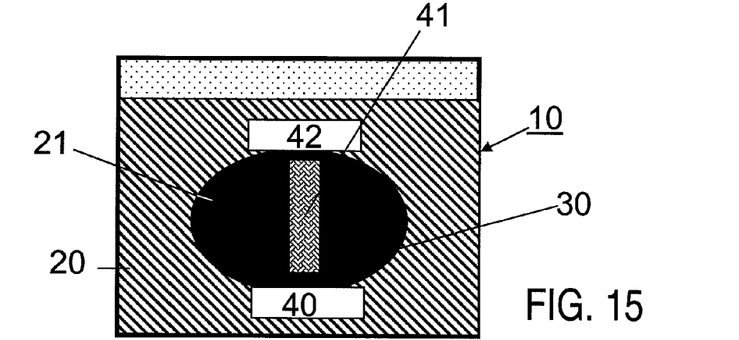

According to FIG. 15, one of the substrate bodies 41 is arranged exclusively in the inner liquid phase 21. Animal islet cells can be cultivated with the cultivation apparatus according to FIG. 15, e.g., on the inside of the boundary surface 30 which grow on the inner substrate body 41 whereas cells of a patient are cultivated on the outside of the boundary surface 30 that are connected to the outer substrate bodies 40, 42. As a result of the cell cultivation a complex structure is created in which the animal islet cells of the environment are surrounded by the human cells of the treated patient and are separated from the environment. The substrate bodies 40, 41 and 42 advantageously stabilize this cell structure.

Figure 16:
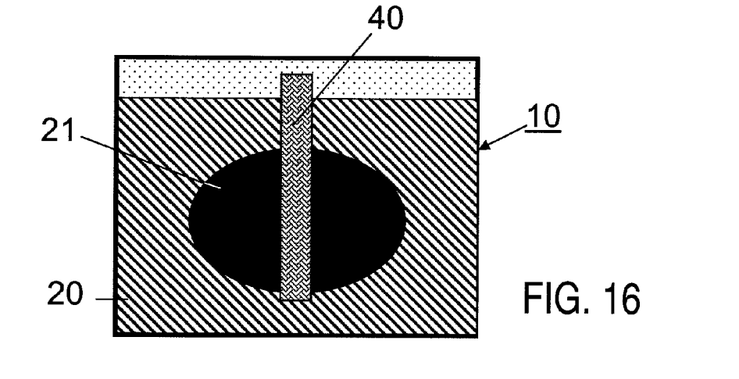

According to FIG. 16, the substrate body 40 can be used to create separate compartments in the culture container 10. Cells of different cell types (not shown) can be cultivated in the separate compartments. The substrate body 40 can have a porous structure and be permeable or semipermeable for liquid or gaseous substances. Furthermore, a substrate body, as is illustrated in an exemplary manner in FIG. 16, can serve for the supply of gas from the gaseous cultivation phase 22 into the liquid cultivation phases 20, 21. The porous substrate body 40 consists, e.g., of a porous ceramic material or of a plastic foam.

Figure 17:
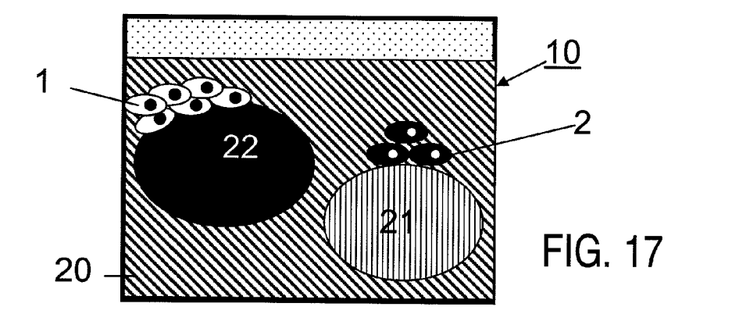
Figure 18:
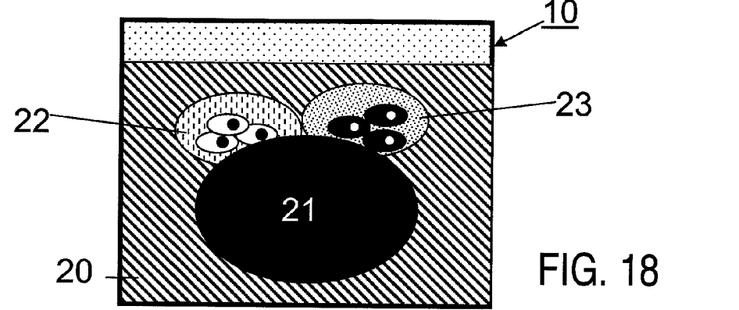

The FIGS. 17 and 18 illustrate further examples for multiphase systems with two or three inner cultivation phases 21, 22, . . . that are surrounded on all sides by an outer cultivation phase 20. According to FIG. 17, cells 1, 2 of different cell types are cultivated on the separate cultivation phases 21, 22, . . . . A separation of the cell types is advantageously achieved with the adjusting of separate cultivation phases 21, 22. The cells 1, 2 of the different cell types are advantageously cultivated separately, during which, however, a chemical connection is given by diffusion through the liquid phase 20. The substances of the liquid phases 21, 22 can be differently selected as a function of the concrete cultivation task and can contain, e.g., nutrient media, hormones, signal factors, differentiation factors, growth factors, etc. The cultivation apparatus according to FIG. 17 can therefore be used as a modification of conventional feeder cultures for stabilizing embryonic stem cells or for differentiating other stem cells.

FIG. 18 shows in analogy with FIG. 8 a three-phase system in which the first inner cultivation phase 21 serves as carrier for the other inner cultivation phases 22, 23 in the outer cultivation phase 20. In analogy with FIG. 17, different substances can be contained in the cultivation phases 22, 23.

Figure 19:
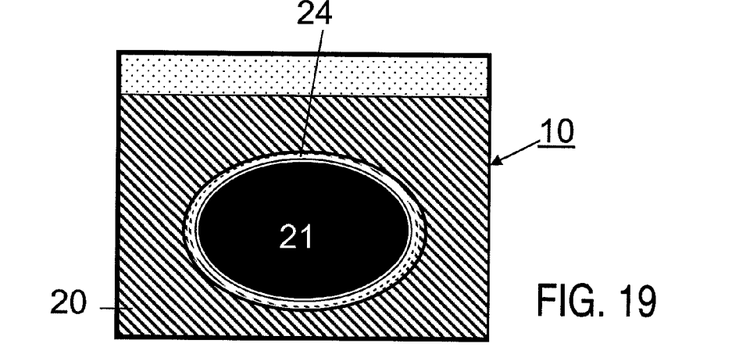

FIG. 19 shows a variant of the invention in which a membrane layer 24 is provided on the boundary surface between the liquid cultivation phases 20, 21. The membrane layer 24 surrounds the inner cultivation phase 21. The cells to be cultivated (not shown) lie on the inside and/or outside of membrane layer 24. The membrane layer comprises a thin layer, e.g., of lipids and/or proteins with a thickness in the sub-mm range. With the membrane layer 24, the application of the invention can be advantageously expanded to cultivation phases with substances that can be mixed with each other. The membrane layer 24 corresponds to the separating layer between differently differentiated cell areas that is given in natural conditions during the cell development in the embryo and in the organism.

Figure 20:
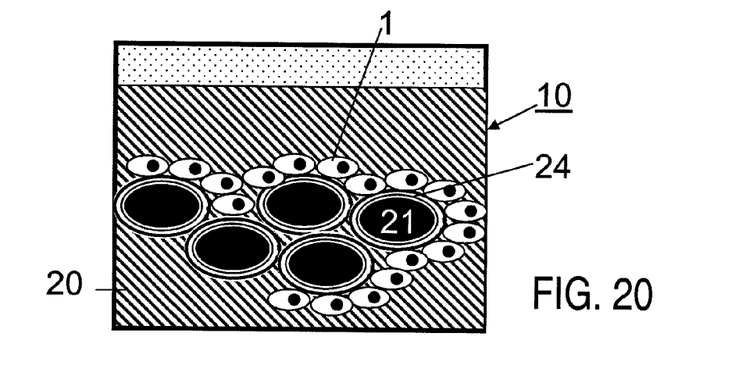

According to FIG. 20, several inner liquid cultivation phases 21 can be arranged in the outer liquid cultivation phase 20 that are surrounded by a membrane layer 24 each. The biological cells 1 can grow, multiply and differentiate on the surface of the group of membrane-surrounded cultivation phases 21. In deviation from the schematic illustration, the membrane-surrounded cultivation phases can be reduced down to microscopically small drops such as, e.g., vesicles or liposomes, that are smaller than or equal to the cells to be cultivated.

Figure 21:
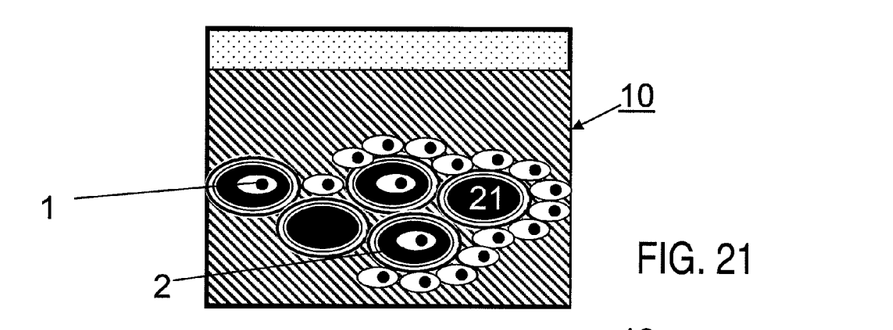

According to FIG. 21, cells 1, 2 can be arranged in individual or all membrane-surrounded cultivation phases 21. The cells 1, 2 can be of the same or different cell types. The cultivation apparatus according to FIG. 21 constitutes a so-called nursing culture.

Figure 22:
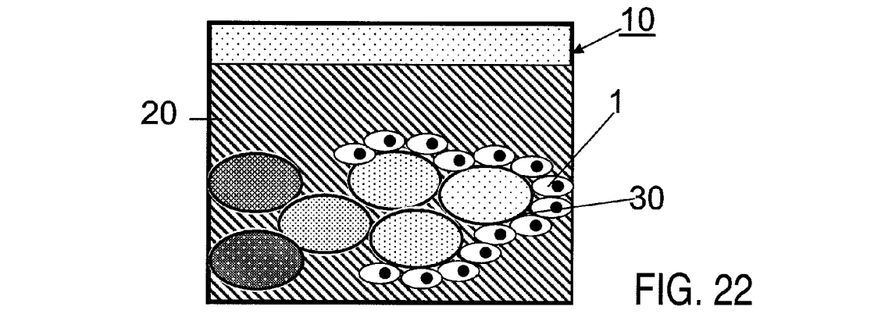

The inner liquid cultivation phases 21 can consist uniformly of certain substances (see, e.g., FIG. 17) or alternatively form a substance gradient within the outer, liquid cultivation phase 20, as is schematically illustrated in FIG. 22. The inner cultivation phases 21 contain, e.g., nutrient media, ions, growth factors, signal factors or the like with different concentrations so that a gradient is produced. Cells 1 on the outer side of the boundary surface 30 to the outer cultivation phase 20 are exposed, corresponding to the course of the gradient, to different concentrations of the corresponding substances. In the cultivation apparatus in accordance with the invention different gradients of physical or chemical culture conditions can be adjusted as a function of the concrete cultivation task. Since the inner cultivation phases 21 can be miniaturized, the gradients can be adjusted two or three dimensionally and optionally continuously. The inner cultivation phases 21 can form, e.g., a planar vesicle carpet with a substance gradient.

Figure 23:
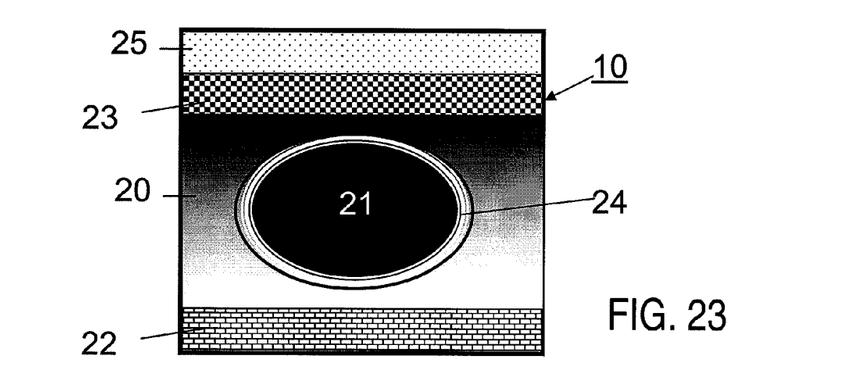
Figure 24:
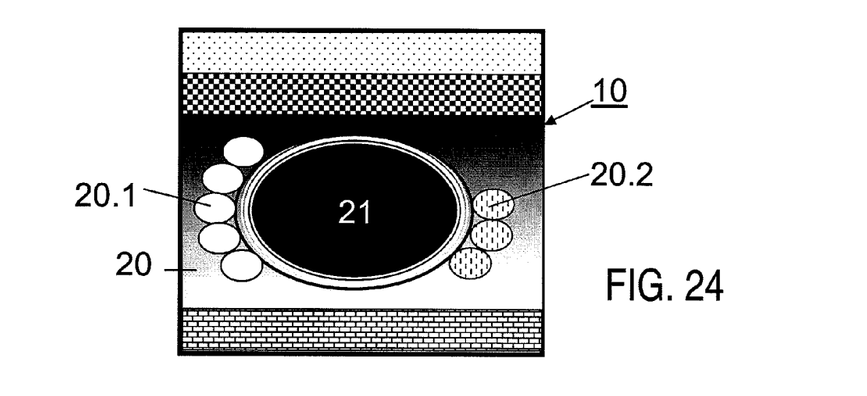
Figure 25:
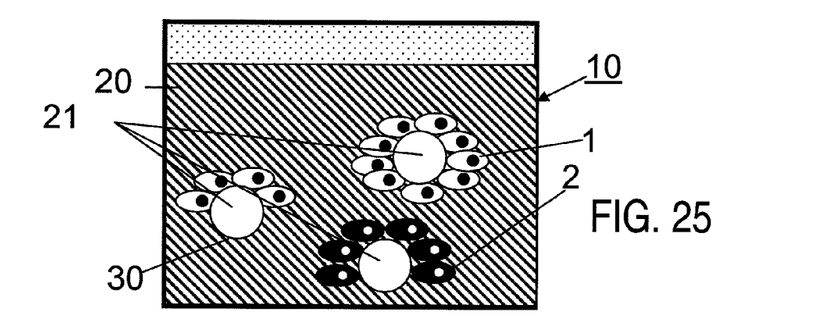

The gradient formation can also be provided in the outer cultivation phase 20, as is schematically illustrated in FIGS. 23 and 24. Four liquid cultivation phases 20 to 23 and a gaseous cultivation phase 25 are provided. The cultivation of the cells (not shown) takes place on the inside and/or outside of the membrane layer 24 between the outer cultivation phase 20 and the inner cultivation phase 21. The additional cultivation phases 22 and 23 are arranged in the culture container 10 in layer form above and below the outer cultivation phase 20 and serve to produce a schematically illustrated gradient in the outer cultivation phase 20. FIG. 24 shows the corresponding adjustment of the cultivation phases, in which nutrient depots 20.1, 20.2 are additionally provided in the outer cultivation phase 20. The additional nutrient depots 20.1, 20.2 serve as further diffusion sources for influencing the chemical culture conditions in the cultivation apparatus.

According to the invention, at least one chemical gradient is preferably produced that is vertically aligned. It can be provided that the vertical gradient slowly dissolves in the course of time or moves through the cultivation phases. The movement can take place, e.g., by buoyancy or sedimentation.

The FIGS. 25 to 28 illustrate a cultivation apparatus in which culture conditions similar to those of the cell cultivation in suspended drops are provided, in which the geometric properties of boundary surfaces 30 between a liquid cultivation phase 20 and at least one gaseous cultivation phase 21 can be selected by the cultivation phase adjustment in accordance with the invention. According to FIG. 25, gas bubbles 21 are inserted as gaseous cultivation phases into the liquid cultivation phase 20 in the culture container 10. The inventors have determined that a sufficient stability for cultivation can advantageously be achieved with the gaseous-liquid system in accordance with FIG. 25. To this end, e.g., the viscosity of the liquid cultivation phase 20 is adjusted so high that the gaseous cultivation phases 21 arranged in the liquid cultivation phase 20 can not migrate to the surface within the cultivation time. The cells 1, 2 are cultivated on the boundary surfaces 30, especially on the outer side of the gaseous cultivation phases 21.

Figure 26:
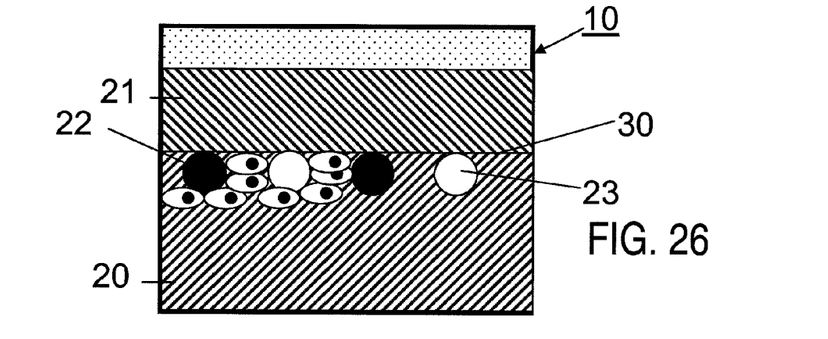

FIG. 26 shows a corresponding structure in a multiphase system with two liquid cultivation phases 20, 21 arranged in layer form, on whose boundary surface 30 liquid (22) and gaseous (23) cultivation phases are provided.

In a corresponding manner, a complex boundary surface is formed on which the cell cultivation takes place. Asymmetric cell cultures like those desired for the stem cell differentiation can advantageously be produced with the cultivation phase adjustment according to FIG. 26.

Figure 27:
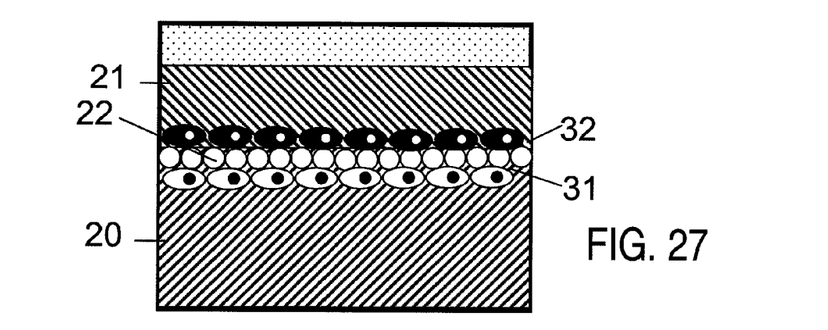
Figure 28:
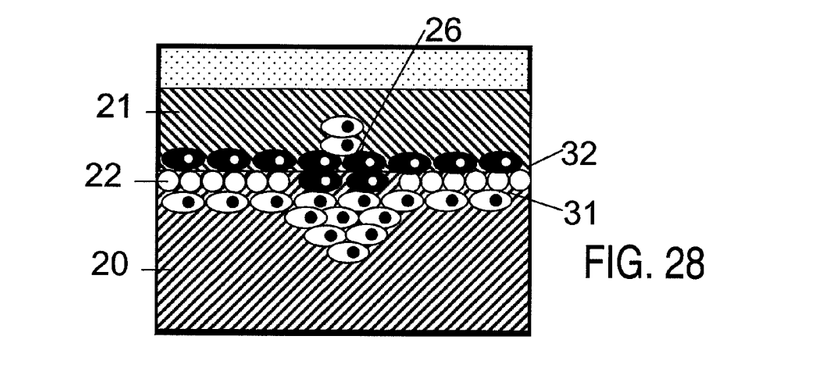

According to a further variant of the invention, a gaseous cultivation phase 22 in the form of a plurality of gas bubbles can be arranged between two liquid cultivation phases 20, 21, as is schematically shown in the FIGS. 27 and 28. Three-phase systems are created in which two boundary surfaces 31, 32 for the cultivation of cells of the same or different type are provided. According to FIG. 28, the layer of the gaseous cultivation phase 22 can comprise interruptions so that cells can be exchanged through a gap 26 between the two sides of the boundary surfaces 31, 32 and grow into each other.

Figure 29:
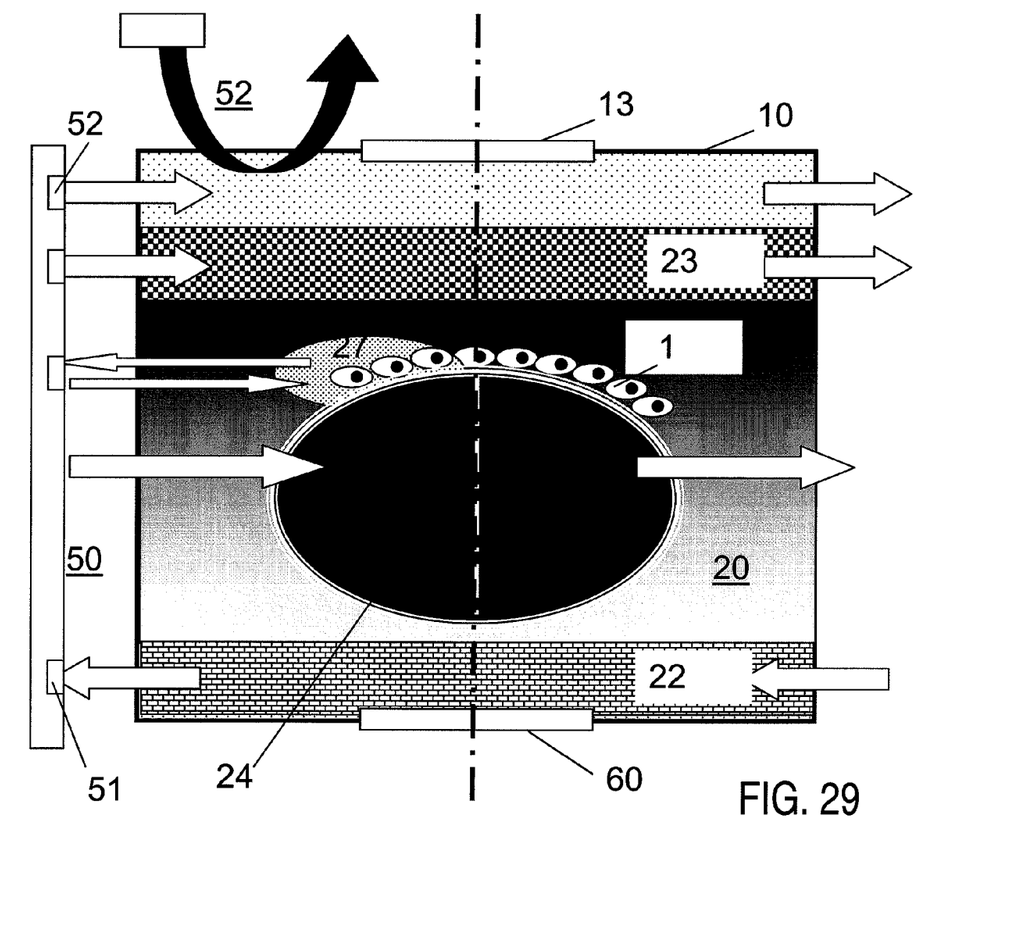
FIG. 29 shows a first embodiment of a cultivation apparatus in accordance with the invention.

FIG. 29 shows an embodiment of the cultivation apparatus 100 in accordance with the invention with a culture container 10 and cultivation phases 20 with further details using the example of the structure according to FIG. 23. The culture container 10 is a receptacle for the liquid or gaseous cultivation phases 20 in the form, e.g., of a beaker glass. An injection apparatus 50 (schematically shown) with at least one liquid injector 51 and at least one gas injector 52 for the supplying of additive substances into the individual cultivation phases is provided. The arrows in FIG. 29 schematically illustrate the exchange of substances from the cultivation phases with the environment. The at least one gas injector 52 serves for the supplying of, e.g., $O_2$ or $CO_2$ and optionally as moistening apparatus for adjusting a certain environmental moisture in the gaseous cultivation phase 26. A schematically illustrated tempering apparatus 60 is arranged on the bottom of the culture container 10. The top of the culture container 10 is closed. An observation window 13 is provided through which the cultivated cells can be observed and optionally illuminated.

The chemical composition of each of the liquid cultivation phases 20 can be adjusted with the at least one liquid injector 51. A gradient can be produced in the middle cultivation phase with the upper and lower cultivation phases in layer form analogously to FIG. 23. The cells 1 to be cultivated grow on the outer surface of the membrane layer 24 and additionally a cultivation phase 27 is optionally provided with a nutrient medium.

FIG. 30 illustrates a further embodiment of the culture container 10 in the form of a cylinder for the cultivation phase adjustment in accordance with the invention. A lower (20) and an upper (21) liquid cultivation phase are provided in a layer form in the culture container 10 that enclose a middle (22) liquid cultivation phase (FIG. 30A). In order to adjust the middle cultivation phase 22 one or more injection lines 14 are used with which the substance of the middle liquid cultivation phase 22 (gas or liquid) and optionally a cell suspension can be introduced into the culture container 10. The other cultivation phases 20, 21 or further cultivation phases can be correspondingly adjusted through injection lines. A closure 15 with a gas diffusion insert 16 is provided on the top of the culture container 10 through which the gaseous cultivation phase 23 can be supplied. The partial image in FIG. 30B shows the top view onto the culture container 10 with the media lines 14 and the closure 15.

The features of the invention disclosed in the above description, the drawings and the claims can be significant both individually and also in combination for the realization of the invention in its different embodiments.

The invention claimed is:

1. A process for cell cultivation of biological cells comprising the steps of:
   a) introducing an outer cultivation phase and an inner cultivation phase into a culture container, wherein the outer cultivation phase surrounds the inner cultivation phase and a curved boundary surface is formed by the outer cultivation phase and inner cultivation phase, and wherein:
      i) the outer cultivation phase is a silicone oil or gel, and the inner cultivation phase is a nutrient medium; or
      ii) the outer cultivation phase is a nutrient medium, and the inner cultivation phase is a silicone oil; and
   b) culturing the biological cells at the curved boundary surface wherein the biological cells are introduced during or after the introducing of the inner cultivation phase.

2. The process according to claim 1, wherein the cultivation phases are formed with pre-determined additive substances with which at least one of a density, a viscosity and a miscibility of the cultivation phases is influenced.

3. The process according to claim 1, further comprising the step of supplying a gas to the biological cells.

4. The process according to claim 1, further comprising the step of producing a phase transition in at least one of the cultivation phases.

5. The process according to claim 1, further comprising the step of fusing the inner and outer cultivation phases.

6. The process according to claim 1, further comprising the step of dividing at least one of the cultivation phases into separate cultivation phases.

7. The process according to claim 1, further comprising the step of providing at least one substrate body in at least one of the cultivation phases.

8. The process according to claim 7, wherein the at least one substrate body is arranged in the inner and outer cultivation phases.

9. The process according to claim 7, wherein the substrate body comprises a gel body, a net, a filament, a textile substrate and/or a foil.

10. The process according to claim 1, further comprising the step of manipulating the biological cells, wherein said manipulating is at least one of removing cells, grouping cells or supplying cells.

11. The process according to claim 1, wherein the container is artificially produced.

12. The process according to claim 1, wherein the container has an inner from that does not shape the boundary surface.

13. The process according to claim 1, wherein the culturing the biological cells comprises forming a cell union or cell aggregate.

14. The process according to claim 1, wherein the inner cultivation phase is injected into the outer cultivation phase.

15. The process according to claim 1, wherein the inner cultivation phase or the outer cultivation phase is silicone oil.

16. A process for cell cultivation of biological cells comprising the steps of:
   a) introducing into a culture container an outer cultivation phase and an inner cultivation phase surrounded by the outer cultivation phase, providing a membrane on a curved boundary surface between the outer cultivation phase and the inner cultivation phase, and wherein:
      i) the outer cultivation phase is a silicone oil or gel and the inner cultivation phase is a nutrient medium; or ii) the outer cultivation phase is a nutrient medium, and the inner cultivation phase is a silicone oil or gel; and b) culturing biological cells at the membrane, wherein the biological cells are introduced during or after the introducing of the inner cultivation phase.

17. The process according to claim 16, wherein the inner cultivation phase is injected into the outer cultivation phase.

18. The process according to claim 16, wherein the inner cultivation phase or the outer cultivation phase is silicone oil.

* * * * *